US008087116B2

(12) United States Patent
Spooner et al.

(10) Patent No.: US 8,087,116 B2
(45) Date of Patent: Jan. 3, 2012

(54) ELECTRIC TOOTHBRUSH

(75) Inventors: Gregory Clegg Spooner, Causeway Bay (HK); Hoss Vong, Causeway Bay (HK)

(73) Assignee: Hayco Manufacturing Ltd., Causeway Bay (HK)

( * ) Notice: Subject to any disclaimer, the term of this patent is extended or adjusted under 35 U.S.C. 154(b) by 1029 days.

(21) Appl. No.: 11/985,091

(22) Filed: Nov. 14, 2007

(65) Prior Publication Data
US 2008/0115300 A1 May 22, 2008

(51) Int. Cl.
*A46B 13/02* (2006.01)
*A61C 17/34* (2006.01)

(52) U.S. Cl. .............................................. 15/22.1; 15/28
(58) Field of Classification Search ................... 15/22.1, 15/28
See application file for complete search history.

(56) References Cited

U.S. PATENT DOCUMENTS 5,226,206 A * 7/1993 Davidovitz et al. ............ 15/22.1

FOREIGN PATENT DOCUMENTS

| DE | 29 40 275 A1 | 4/1981 |
| DE | 198 02 904 A1 | 7/1999 |
| EP | 0 968 686 A1 | 1/2000 |
| WO | WO 99/63905 | 12/1999 |
| WO | WO 2005/058191 A1 | 6/2005 |

OTHER PUBLICATIONS

Search Report from UK Patent Office on Priority Application HK06112762.5 (6 pages), dated Jan. 26, 2007.

\* cited by examiner

*Primary Examiner* — Randall Chin
(74) *Attorney, Agent, or Firm* — Renner, Kenner, Greive, Bobak, Taylor & Weber

(57) ABSTRACT

The invention relates to a mechanism for driving the head of an electric toothbrush. The mechanism includes a cam 20 rotatably driven by a motor 10 and an elongate transfer mechanism 30 having a receiver 40 for receiving the cam at one end and a mechanism for transferring oscillatory motion to a toothbrush head 60 at the other end thereof. Cam 20 has a projecting head 23 which is received in a substantially rectangular aperture 41 of the receiver 40. The long side of the substantially rectangular aperture has a length equal to or greater than the diameter of the circular motion of the projecting head 23, the short side has a length less than the long side of the rectangular aperture. Thus, in use, circular motion of the projecting head of the cam is converted into oscillatory pivoting motion of the transfer member 30 by action of the projecting head 23 against the short sides of the substantially rectangular aperture 41. A tooth and gear arrangement for converting pivoting motion of the transfer member 30 into rotational motion of the toothbrush head 60 is also described.

9 Claims, 6 Drawing Sheets

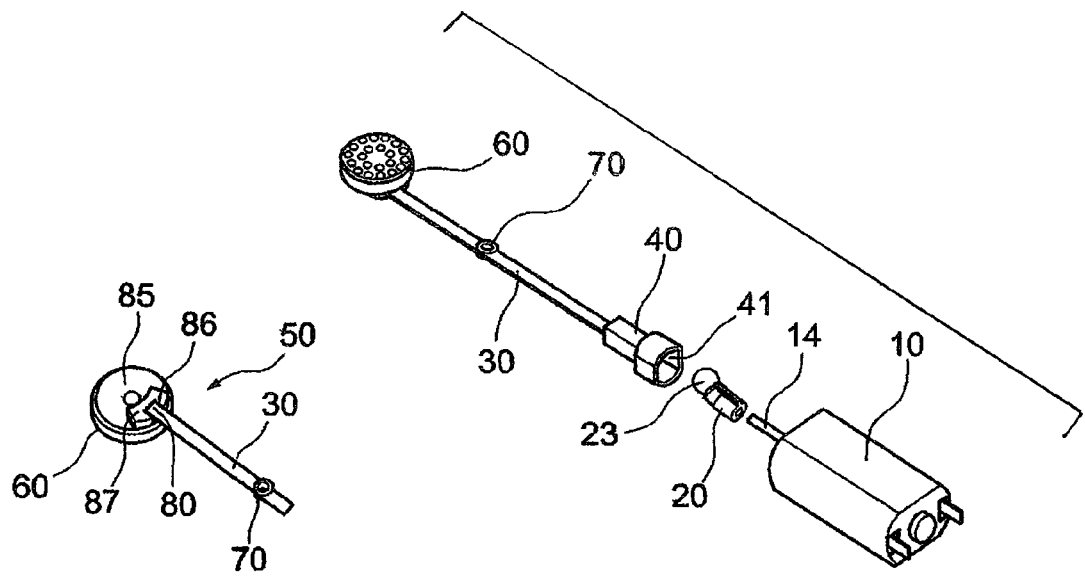
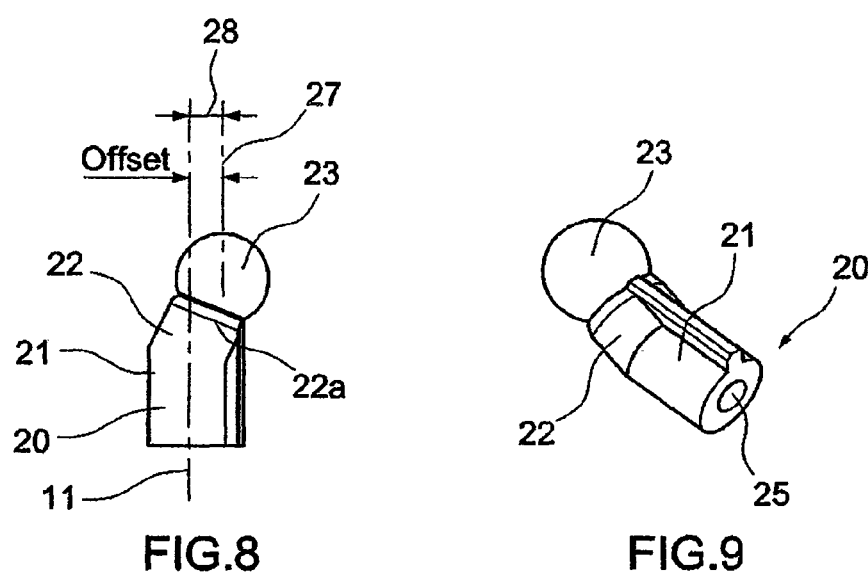

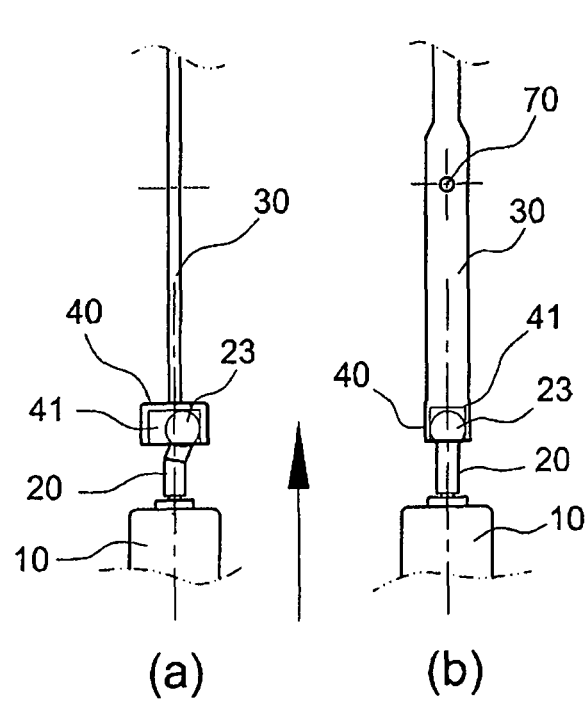
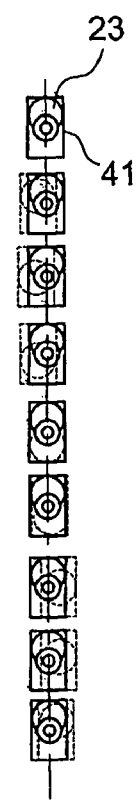
FIG. 15
FIG. 10
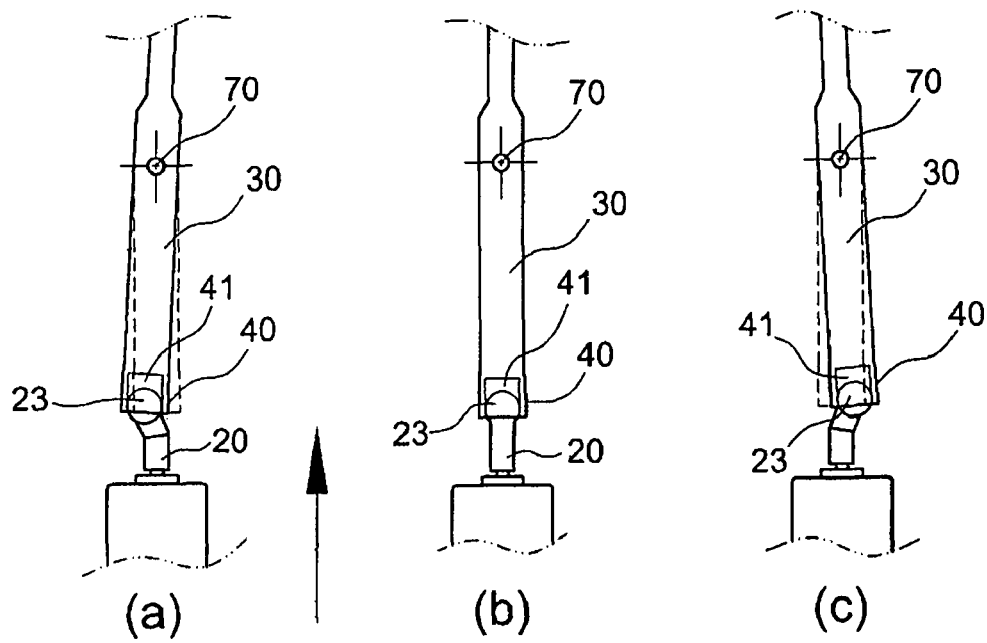
FIG. 14

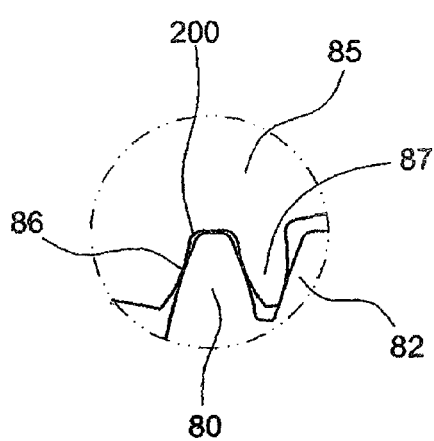
FIG.12
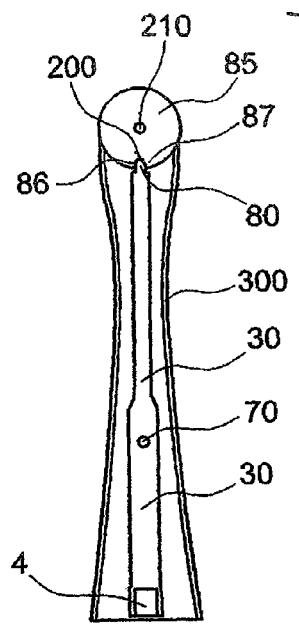
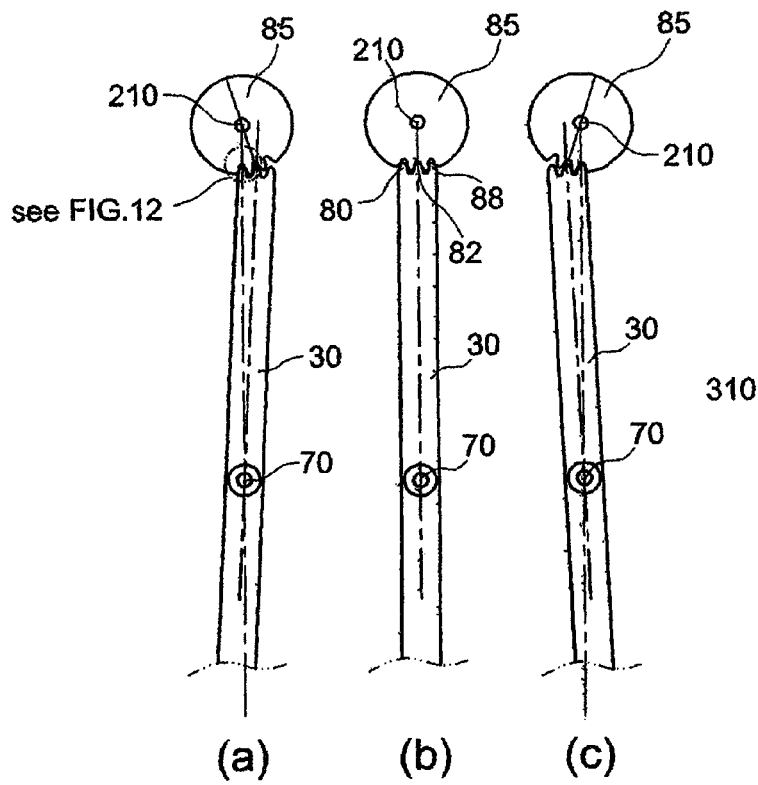
FIG.11
FIG.13

ELECTRIC TOOTHBRUSH

The present invention relates to an electric toothbrush and a head driving mechanism for an electric toothbrush.

In general, electric toothbrushes have a motor, which is usually located in the handle, and a mechanism for transferring rotational motion of the motor to rotational or reciprocating movement of the toothbrush head for cleaning teeth. It is necessary for the components of the mechanism to endure sustained movement over a period of time. The present invention aims to provide a mechanism which is simple, efficient, yet compact.

Accordingly, at its most general, one aspect of the present invention proposes an elongate transfer member for transferring motion to a toothbrush head, said transfer member having a receiver with an aperture of receiving the projecting head of a cam which is coupled to the motor. The aperture has a first dimension with a length greater than or equal to the diameter of the circular path of the projecting head and a second dimension which is smaller than the first dimension. This way the circular motion of the cam's projecting head is converted into side to side oscillatory motion of the elongate transfer member due to action of the projecting head on the wall's bounding the second dimension of the aperture.

A first aspect of the present invention preferably provides an electric toothbrush having:—
  a motor;
  a cam rotatably driven by the motor and having a projecting head offset from the cam's axis of rotation; whereby in use the projecting head of the cam describes a circular motion around the cam's axis of rotation; an elongate transfer member for transferring motion from the cam to a toothbrush head, said transfer member having first and second ends, the first end having a receiver for receiving the projecting head of the cam, the second end having or being linked to a mechanism for transferring oscillatory motion to a toothbrush head;
  said receiver having an elongate aperture for receiving the projecting head of the cam, the length of the aperture being equal to or greater than the diameter of the circular motion of the projecting head of the cam, the width of the aperture, perpendicular to said length, having a length less than the length of said aperture; whereby in use circular motion of the projecting head of the cam is converted into oscillatory motion of the transfer member by action of the projecting head of the cam against the short sides of the elongate aperture.

The mechanism is such that the oscillatory motion of the transfer member is substantially planar or linear (i.e. substantially confined to one plane). In this way the width of the aperture can be made relatively small, thus allowing the elongate transfer member to be relatively thin. Furthermore, the toothbrush is comfortable for the user because motion of the transfer member is confined to one plane.

Preferably the width of the aperture is just large enough to accommodate the projecting head of the cam. In this way the receiver is made as thin as possible, while maximizing the extent of translational motion transferred to the transfer member.

Preferably the elongate transfer member is arranged to pivot at a pivot point between its first and second ends, whereby circular motion of the projecting head of the cam is converted to oscillatory pivoting motion of the transfer member. This is a convenient way of transferring the side to side motion to the second end of the elongate transfer member.

Preferably the electric toothbrush further comprises a toothbrush head linked to said mechanism for transferring oscillatory motion to a toothbrush head. Usually the toothbrush head will be removable, so it can be replaced when the bristles are worn. Thus the toothbrush head is not considered to be an essential part of the first aspect of the present invention, as the toothbrush is essentially still a toothbrush even when its head has been removed.

The projecting head of the cam may be cylindrical or substantially spherical. This eliminates sharp edges, thus reducing wear and tear and facilitating smooth movement of the projecting head in the elongate aperture.

Preferably the projecting head is substantially spherical; this may eliminate the need for clearance between the projecting head and elongate aperture, thus reducing noise, wear and tear. For example the projecting end of the cam may comprise a ball.

Preferably the motor has a shaft, which is connected directly to the cam, such that the axis of rotation of the motor and the cam are the same. This gives a simple and robust connection between the cam and the motor. The attachment of the motor shaft to the cam may for example be integral, or by means of a spline.

Preferably the mechanism for transferring oscillatory motion to a toothbrush head comprises an arrangement of interacting or intermeshing gear teeth. The arrangement comprises a first body having at least one tooth and a second body having at least one tooth or an aperture for engaging said tooth of the first body, whereby movement of the tooth or aperture causes at least one of said bodies to rotate. Preferably one of said bodies is a drive wheel for driving rotation of a toothbrush head.

Preferably the involute teeth lie on involute curves (i.e. an involute profile). When the teeth have involute curves, their relative rates of rotation may be constant as they rotate, thus minimizing vibration, noise, wear and tear.

Preferably the transfer member has a first tooth at its second end which engages with an aperture between two teeth of a drive wheel which is connected to, or forms part of, the toothbrush head; whereby oscillating motion of said first tooth causes rotating oscillatory motion of the drive wheel and toothbrush head. The drive wheel has at least one tooth or at least one aperture for engaging a tooth of the transfer member. In one preferred embodiment the drive wheel only has two teeth. The two teeth of the drive wheel need not be projections and may be formed by the opposing sides of an aperture in the drive wheel.

A second aspect of the present invention preferably provides an electric toothbrush having:—
  a motor;
  an elongate pivoting member arranged to pivot about a pivot point;
  a mechanism for translating rotational motion of the motor into oscillatory pivoting motion of the pivoting member;
  a toothbrush head and a mechanism comprising an arrangement of interacting gear teeth, arranged between the elongate pivoting member and the toothbrush head, said mechanism being arranged for translating oscillatory pivoting motion of the pivoting member into oscillatory rotational motion of the toothbrush head; said teeth having involute curves.

This is a simple mechanism for transferring the motion to the toothbrush head, which enables the pivoting member and mechanism to be kept comparatively flat so as to minimize the space taken up. The involute shape of the teeth may help to minimize vibration, noise and/or wear and tear.

Preferably the transfer member has a first tooth at its second end which engages with an aperture between two teeth of a drive wheel which is connected to, or forms part of, the toothbrush head; whereby oscillating motion of said first tooth causes rotating oscillatory motion of the drive wheel and toothbrush head. In one preferred embodiment the drive wheel only has two teeth.

The second aspect of the present invention may have any of the preferred features of the first aspect of the invention, which are discussed above.

A third aspect of the present invention preferably provides an electric toothbrush having:—
- a motor;
- a cam rotatably driven by the motor and having a projecting head offset from the cam's axis of rotation; whereby in use the projection head of the cam describes a circular motion around the cam's axis of rotation;
- an elongate transfer member for transferring motion from the cam to a toothbrush head, said transfer member having first and second ends, the first end having a receiver for receiving the projecting head of the cam, the second end having or being linked to a mechanism for transferring oscillatory motion to a toothbrush head;
- said receiver having an aperture for receiving the projecting head of the cam, the aperture having a first dimension extending in a first direction perpendicular to the axis of rotation of the cam and a second dimension extending in a second direction perpendicular to said first direction and said cam axis; the first dimension having a length equal to or greater than the diameter of the circular motion of the projecting head of the cam, the second dimension having a length less than that of the first dimension; whereby in use circular motion of the projecting head of the cam is converted into linear oscillatory motion of the transfer member by action of the projecting end of the cam against the short sides of the substantially rectangular aperture.

This enables the second dimension to be minimized in order to keep the elongate transfer member relatively thin.

Preferably the first dimension is just large enough to accommodate the projecting head of the cam.

Preferably the aperture is substantially rectangular and the first dimension corresponds to the long side of the rectangle and the second dimension to the short side of the rectangle.

Preferably the elongate transfer member is arranged to pivot at a pivot point between its first and second ends, whereby circular motion of the projecting head of the cam is converted to oscillatory pivoting motion of the transfer member and wherein said first dimension extends in a direction substantially parallel to the axis of pivoting of the elongate transfer member.

Embodiments of the present invention will now be described, by way of example only, with reference to the accompanying drawings in which:—

FIG. 4 is a plan-view of a mechanism for transferring motion from an elongate member to a toothbrush head;

FIG. 5(a)-(d) are schematic diagrams of the toothbrush in operation showing the position of the transfer member of the toothbrush head and the oscillation angles in various positions;

FIG. 6 is a diagram showing components of an electric toothbrush according to a second embodiment of the present invention;

FIG. 7 is a diagram showing the back of the toothbrush head and the upper part of the transfer member of the toothbrush according to the second embodiment of the present invention;

FIG. 8 is a side view of a cam for use in the second embodiment;

FIG. 9 is a perspective view of a cam for use in the second embodiment;

FIG. 10 is a schematic plan view showing the relative positions of the projecting head of the cam and the aperture of the receiver at various points around the circular path of the cam;

FIGS. 11(a)-(c) show an alternative arrangement using engaged gear teeth for transferring oscillatory motion to a toothbrush head;

FIG. 12 is an enlarged view of a portion of FIG. 11 showing the engagement of the gear teeth;

FIG. 13 shows schematically the toothbrush components including its casing; and

FIGS. 14(a)-(c) show how the transfer member pivots due to action of the projecting head of the cam; and FIGS. 15(a)-(b) are views of both sides of the toothbrush showing the cam and transfer member.

Figure 1:
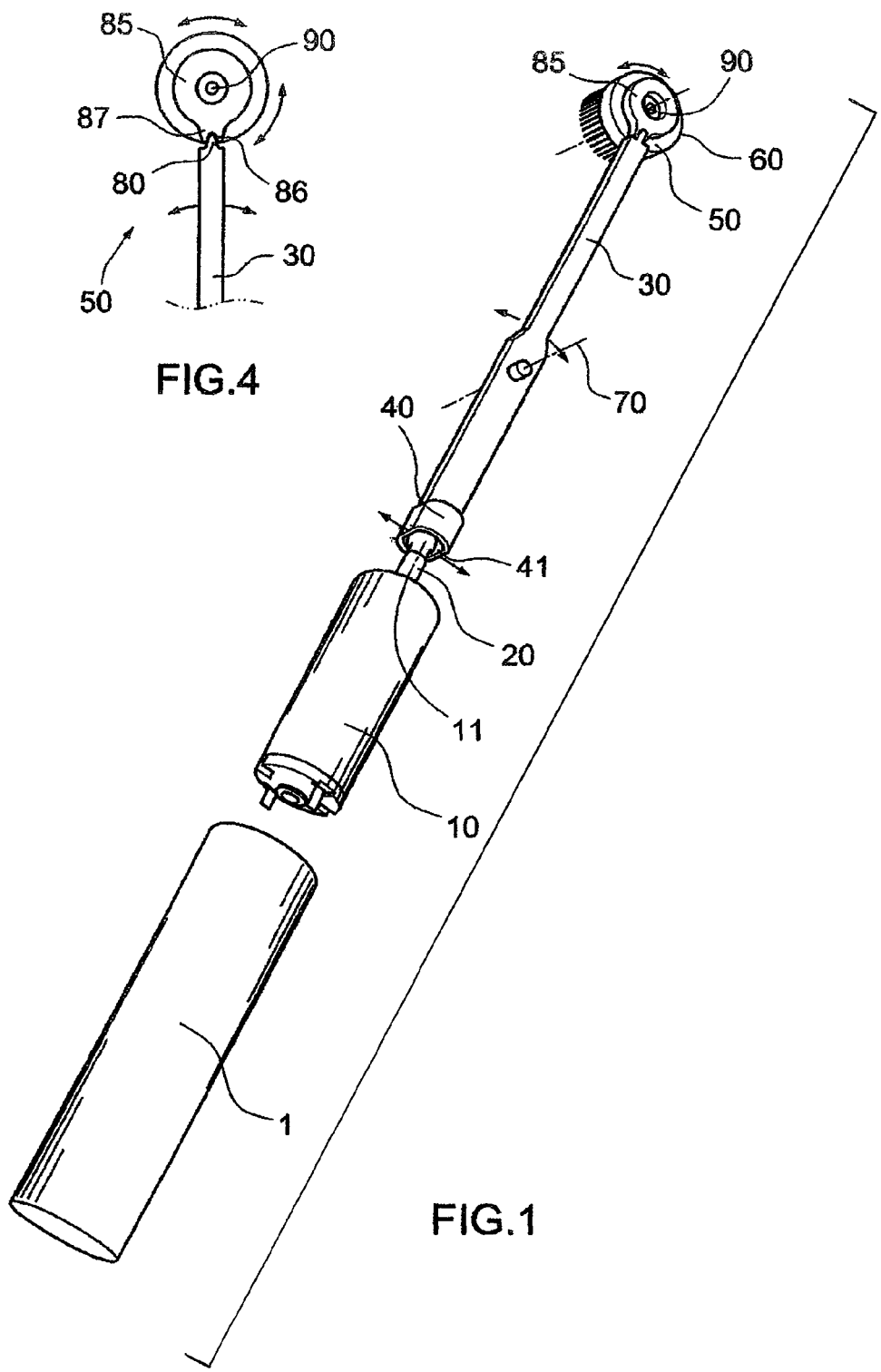
FIG. 1 shows a toothbrush in accordance with an embodiment of the present invention.

FIG. 1 shows the main internal operative components of an electric toothbrush according to a first embodiment of the present invention, with the external casing omitted. The electric toothbrush comprises of a battery 1, a motor 10, a cam 20 and an elongate transfer member 30 which has a receiver 40 for receiving the cam 20 at a first end and forms part of a mechanism 50 for transferring motion to a toothbrush head 60 at a second end thereof.

The battery 1 is electrically connected to the motor 10 and supplies the motor with electrical power. In this embodiment the battery 1 and the motor 10 are cylindrical in shape and housed together within the toothbrush's handle.

Figure 2:
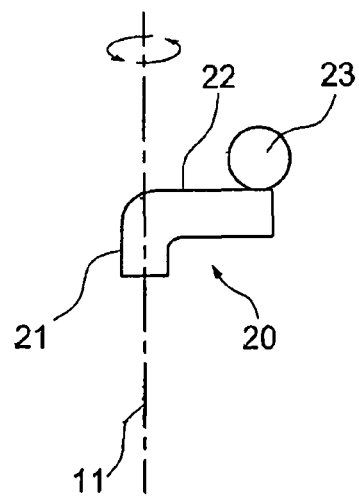
FIG. 2 is a side view of a cam having a projecting head offset from its axis of rotation.

The cam 20 is shown in more detail in FIG. 2. The cam 20 has a first portion 21 which is in the line with and connected directly to the shaft (not shown) of the motor 10. The attachment of this portion 21 of the cam to the motor shaft may be an integral connection, or by means of a spline or other known connecting means. This first part 21 of the cam rotates co-axially with the motor shaft when the motor 10 is switched on. The axis 11 of the motor shaft is shown in both FIG. 1 and FIG. 2 by dotted lines. In addition to the first portion 21, the cam has a second portion 22 which bends in a L-shape to one side and extends radially outward from the axis of rotation 11. A ball bearing 23 is attached to an upper surface of the radially extending portion 22 and acts as a "projecting head" of the cam. Thus when the cam rotates, the projecting head 23 describes a circular path around the rotational axis 11 of the cam and the motor shaft. The above described arrangement is by way of example only and as will be apparent to a person skilled in the art, the cam may be manufactured by other means or other components and may have a different type of connection to the motor. The important point is that the projecting head 23 describes a circular motion around the cam's rotational axis, which it is radially offset from.

The elongate transfer member 30 has a receiver 40 for receiving the projecting head 23 of the cam 20. In this embodiment the receiver 40 is formed by an enlarged flange positioned towards the first end of the elongate transfer member 30. The receiver 40 has an internal aperture 41 which has a substantially rectangular shape (in cross section on a plane perpendicular to the axis of rotation of the cam 20). The projecting head 23 is received inside the aperture 41, but the other parts of the cam 21, 22 are not received inside the aperture 41.

Figure 3:
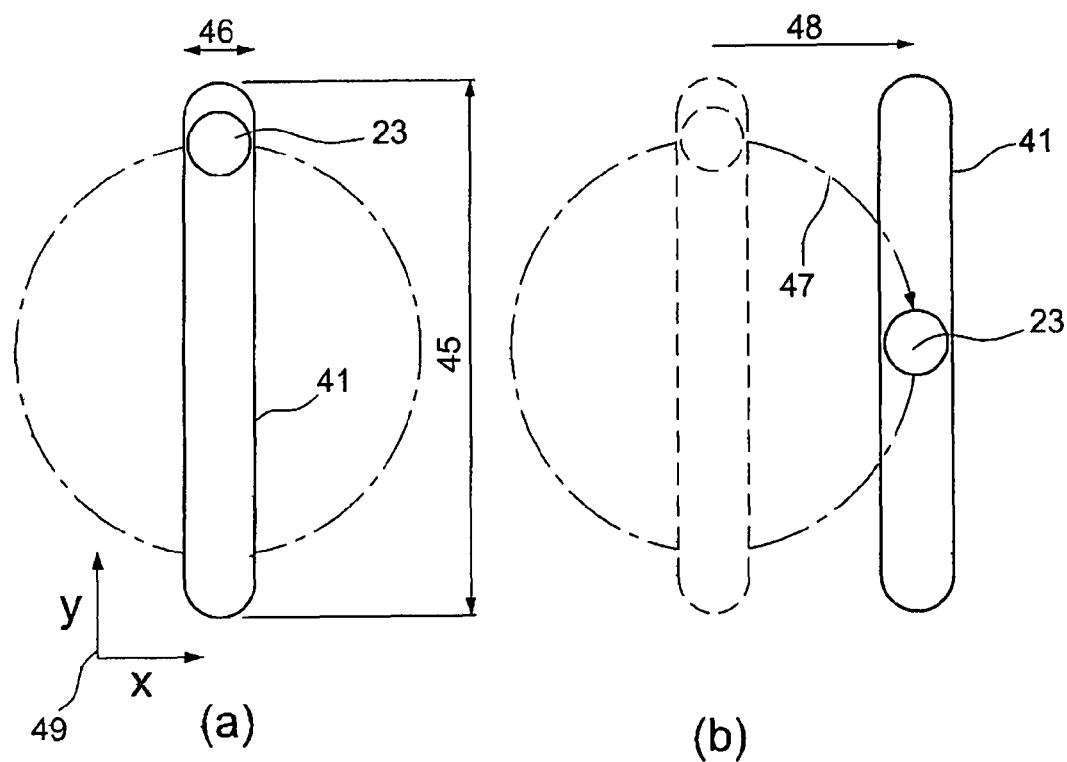
FIG. 3(a) is a schematic diagram showing the relative positions of the projecting head of the cam and the aperture of the receiver in a first position.
FIG. 3(b) is a schematic diagram showing the relative positions of the cam and the aperture of the receiver in a second position.

The relationship between the projecting head 23 of the cam and the aperture 41 of the receiver 40 is shown in more detail in FIG. 3, which it is schematic plane view. In FIG. 3 (a) the projecting head 23 of the cam is in a first position near the top of its circular path. The circular path described by the projecting head of the cam, when the toothbrush is in use and the motor is turned on is shown by the dotted lines. As can be seen in FIG. 3 (a) the aperture 41 has a first dimension 45 (the long side of the rectangle described by the aperture) and a second dimension 46 (the short side of the rectangle). In the first position shown in FIG. 3 (a) the projecting head 23 is towards one of the short sides of the aperture. The projecting head's edges abut against the long sides of the aperture because the rectangular aperture has a second dimension 46 only just large enough to accommodate the projecting head 23. However, the projecting head 23 does not abut against the short sides of the aperture 41 because the aperture has a first dimension 45 long enough to accommodate the entire range of movement of the projecting head in the y-plane. There may be a little play between the projecting head 23 and the long sides of the aperture so that friction does not prevent the projecting head 23 from moving along the aperture.

In FIG. 3(b) the projecting head 23 has advanced a quarter of the way around its circular path relative to the first position shown in FIG. 3(a). In this second position the projecting head 23 has moved away from end and towards the center of the substantially rectangular aperture 41. In FIG. 3(b) the previous first position of the projecting head 23 and aperture 41 is shown in the dotted and dashed lines. The remaining portion of the circular path to be followed by the projecting head 23 is shown in dashed lines and its motion from the previous first position to its second position is shown by arrow 47. As the projecting head 23 abuts against the long edges of the rectangular aperture, the receiver 40 has moved in the direction shown by arrow 48, i.e. in a direction substantially perpendicular to the long side of the rectangular aperture and perpendicular to the axis of rotation of the cam. However, there is no up and down motion of the receiver 40 in the direction 49 (parallel to the long sides of the rectangle) because the aperture 41 is long enough that the projecting head 23 does not push against the small side ends of the aperture even when the projecting head is at the maximum extent in the y direction along its circular path. Thus, the circular motion of the cam 20 is converted into a oscillating or reciprocating motion of the receiver 40 in the x direction only. There is substantially no translational motion of the receiver 40 in the y direction. Due to the relatively close fit of the aperture 41 and the projecting head 23 in the second dimension 46 (the short side of the rectangle), the transfer member 30 above the receiver 40 can be made comparatively slim in the x-direction, as can the surrounding casing. Furthermore, movement of the transfer member is minimized as there is substantially no movement in the y-direction. This provides a more comfortable experience for the user of the toothbrush, as the part of the toothbrush placed in their mouth is thinner and the motion is confined to one plane. This is especially advantageous if the toothbrush is to be used by infants, who have small mouths.

The transfer member 30 has a pivot 70 positioned between its two ends. The pivot is rotatably attached to or mounted in a casing (not shown), which surrounds the elongate transfer mechanism. The casing may be made slim in the y direction, as the motion of the transfer member 30 is planar and substantially confined to the x-z plane, where z is the axis of the rotation of the cam). The receiver 41 is fixably attached to transfer member 30, so the receiver's oscillatory translational motion in the x direction (shown by the arrows in FIG. 1) causes the elongate transfer member 30 to pivot around its pivot point 70. As the elongate transfer member pivots, it may be called a "pivoting member". The motion of the pivoting of the second end of this member 30 of the second end is converted into a rotational oscillation of the toothbrush head 60 by a mechanism 50 which will now be described.

The mechanism 50 for transferring an oscillatory motion to the toothbrush head 60 is shown in more detail in FIG. 4. FIG. 4 is a plan-view of the end of the toothbrush head and the top part of the pivoting member 30. The mechanism 50 in essence comprises an arrangement of interacting gear teeth, in which there is just a single tooth on the transfer member meshed with a pair of teeth on the head. More particularly, a first tooth 80 projects from the second end of the transfer member 30 and engages an aperture between two teeth of 86, 87 of a driving wheel 85. The arrangement of meshed teeth is such that they have involute curves, as the teeth are shaped to allow more than one point of engagement as they move relative to each other. As the first tooth 80 moves back and forth with the pivoting of the pivot member 30, as shown by the arrows in FIG. 4, the drive wheel 85 and toothbrush head 60 rotate back and forth by engagement of the gear teeth 80, 86, and 87. The drive wheel and toothbrush head are rotatably mounted on a casing (not shown) of the upper part of the toothbrush which surrounds the pivoting member 30. The above arrangement is given by way of example only and could be modified, as will be apparent to a person skilled in the art, for example by providing two teeth and an aperture on the pivoting member 30 and only a single tooth on the drive wheel 85, or by placing the tooth 80 at a location removed from but close to the very end of pivot member 30. The drive wheel 85 rotates about an axis 90 as shown in FIGS. 1 and 4. It may form an integral part of the toothbrush head 60, or be fixably attached thereto. Thus rotation of the drive wheel 85 causes rotation of the toothbrush head 60.

It may, from time to time, be necessary to replace the head of the toothbrush when the bristles wear out. Several designs are possible to achieve this. For example, the whole upper portion, including head 60, drive wheel 85 and transfer rod 30 and its casing could be replaced. Alternatively, the head and drive wheel could detach and be replaced, or the toothbrush head 60 could be detachably fixed to the drive wheel 85, so only the head 60 need be replaced.

Figure 5:
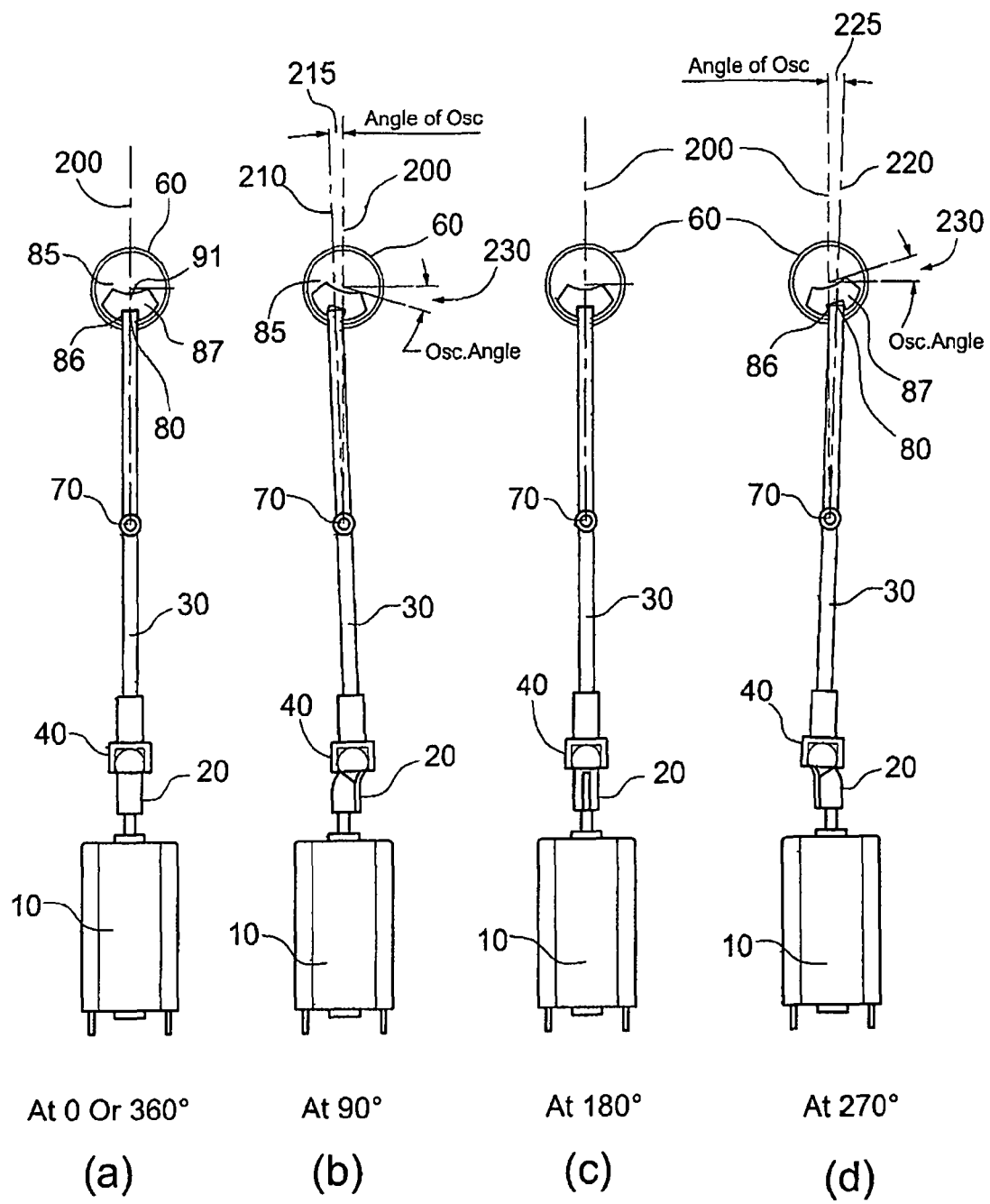

FIG. 5 is a schematic view showing the toothbrush in operation, as seen from behind. FIG. 5 provides a snapshot of the positions of the elongate transfer member 30 and toothbrush head 60 in four different positions (a)-(d). In FIG. 5 (a) the cam's projecting head (shown in dotted lines inside receiver 40) is in a central position corresponding to that of FIG. 3(a). Accordingly, the elongate transfer member 30 is approximately perpendicular to the toothbrush handle. The central axis of the elongate member 30 is therefore aligned with the toothbrush axis, shown by the dotted line 200 in FIG. 5(a).

In FIG. 5(b) the projecting head of the cam 20 has moved to the right (and is 90° around its circular path, corresponding to the position in FIG. 3(b)). Accordingly, the elongate member 30 pivots about the pivot point 70 and its upper end moves to the left causing the toothbrush head 60 to rotate clockwise due to engagement of the tooth 80 with teeth 86 and 87. The angle 215 between the central axis 210 of the elongate member 30 and the perpendicular 200 in this 90 degrees position is shown as angle 215 in FIG. 5(*b*). The corresponding oscillation angle 230 of the toothbrush head is also shown.

FIG. 5(*c*) shows the toothbrush when the projecting head of the cam has moved 180 degrees around its circular path. It is again in a central position and so the elongate transfer member 30 is not pivoting and it is once again perpendicular to the handle. It is aligned with the toothbrush axis 200 as shown in FIG. 5(*c*).

In FIG. 5(*d*) the projecting head of the cam has moved 270 degrees around its circular path and is to the left of the central axis. This causes the upper part of the transfer member 30 to pivot to the right and a corresponding anti-clockwise rotation of the toothbrush head 60 caused by the engagement of tooth 80 with teeth 86 and 87 of the toothbrush head. The angle of oscillation 225 of the elongate member 30 is shown together with the angle of oscillation 230 of the toothbrush head.

FIG. 6 is an exploded view showing the components of an electric toothbrush according to a second embodiment with the present invention. The same reference numerals are used for the same parts as in the first embodiment. The electric toothbrush of the second embodiment has a battery (not shown) which attaches to a motor 10, a cam 20 having projecting head 23, a receiver 40 with aperture of 41 at a first end of elongate transfer member 30 and a toothbrush head 60. The elongate transfer member 30 has a pivot point 70 as described for the first embodiment. The differences will now be described.

FIG. 7 shows in detail the top part of the elongate transfer member 30 and the toothbrush head 60 as seen from the back. There is a tooth and gear arrangement 50, as in the first embodiment. As can be seen, the second end of the elongate transfer member 30 acts as the first tooth 80. Unlike in the first embodiment, the first tooth 80 is not formed by a point or protrusion from the end of member 30, but rather by the rectangular end of the member 30 which itself acts as the first tooth 80. Teeth 86 and 87 of the drive wheel 85 are formed as projections of a member 91 on the drive wheel 85 and an aperture is formed in the gap between them. This aperture between the teeth 86 and 87 receives the end 80 of transfer member 30, which acts as a tooth. The drive wheel 85 only has two teeth 86 and 87 and is attached to or alternatively forms an integral part of the back of the toothbrush head 60. In an alternative configuration the member 91 may be circular and have a single aperture for receiving the first tooth 80. In that case the two teeth of the drive wheel are not projecting from member 91, but rather are formed by the opposing sides of the aperture in member 91. The drive wheel 85 need not necessarily be a separate part from the toothbrush head 60, it may for example be an integral part formed by moulding on the back of toothbrush head 60.

The cam used in the second embodiment is shown in more detail in FIGS. 8 and 9. FIG. 8 is a side view and the rotational axis of the cam 11 is shown by a dotted line. The cam 20 has a first portion 21 which is in line with the rotational axis 11, and a second portion 22 which extends off at an angle to the side of the first portion 21. The second portion 22 of the cam has an end with a flat surface 22*a* on which is mounted a ball which acts as a projecting head 23 of the cam. Line 27 in FIG. 8 shows the center of the ball and is used to illustrate the offset 28 between the projecting head 23 and the rotational axis 11 of the cam. FIG. 9 is a perspective view which shows the cam in more detail. It can be seen that the first part of the cam 21 has a central aperture 25 for receiving a shaft 14 of the motor 10. When the toothbrush is assembled the shaft 14 is inserted into this aperture 25 so that when the motor is switched on, the cam 20 rotates in concert with the shaft 14.

FIG. 15 shows views of the side of the cam 20 and the transfer member 30 of the first and second embodiment. FIG. 15(*a*) is of the long side of the aperture 41 of the receiver 40 and it can be seen that this side of the rectangular aperture is larger than the diameter of the projecting head 23. FIG. 15(*b*) is showing the short side of the rectangle of the receiver's internal aperture 41. It can be seen that the short side of the aperture 41 is just large enough to accommodate the projecting head 23 of the cam. Thus movement of the projecting head 23 of the cam in the direction along the long side of the aperture 41 does not cause the receiver 40 to move. However, movement of projecting head 23 of the cam in the direction along the short sides of the internal aperture 41 does cause the receiver 40 to move. This is shown in FIG. 14.

As can be seen in FIG. 14(*a*), the projecting head 23 of the cam is disposed to the left of the rotational axis of the cam 20 in the direction along the short side of the internal aperture 41. This causes the receiver 40 to move towards the left. Consequently, the transfer member 30 pivots about its pivot point 70. In FIG. 14(*b*) the projecting head 23 is in a central position with respect to the axis of rotation of the cam 20 when looking at a plane parallel to the short sides of the internal aperture 41. Therefore, the receiver 40 is not displaced and the transfer member 30 is in line with the rotational axis of the cam. (The projecting head 23 is of course off-set from this central axis in the direction along the long side of the internal aperture 41, however this does not cause the receiver 40 to move because there is space inside the aperture 41 for the projecting head 23 to move in that direction). FIG. 14(*c*) shows the situation when the projecting head has moved to the right of the rotational axis in the direction along the short sides of the aperture 41, thus causing the receiver 40 to move towards the right and the transfer member 30 to pivot.

FIG. 10 is a top-down plan view showing the relative positions of the projecting head 23 of the cam and the internal aperture of the receiver at various points around the circular path of the projecting head 23 of the cam.

FIG. 11 shows an alternative arrangement for the mechanism 50 for transferring oscillatory motion to a toothbrush head. Again, an arrangement of gear teeth is used. The pivoting transfer member 30 has three teeth, 80, 82, 88 at its upper end (see FIG. 12 for the detail), while the drive wheel 85 has two teeth, 86 and 87. The cooperating teeth lie on involute curves. That is, the teeth have an involute shape or profile. This involute profile provides efficient motion transfer between the transfer member 30 and the drive wheel 85. This multiple tooth and gear mechanism may be used in any of the embodiments which have been described.

FIG. 13 shows the casing 300 and 315 of the toothbrush, which has previously been referred to but not shown in the diagrams. The casing may be used on any of the embodiments which have previously been described. The casing preferably has two parts: first part 310 forming the handle and used for containing the battery 1, motor 10 and preferably also the cam 20; and a second part 300 for containing the transfer member 30 supporting the toothbrush head 60 and drive wheel 85. The casing 310, 300 may be made of plastic, or any suitable material and is hollow so that it can contain the aforementioned parts. Upper casing 300 can be conveniently mounted on and/or attached to a shoulder 315 of the lower handle casing 310. As the transfer member 30 is very thin and only pivots in a single plane, the transfer member 30, its casing 300 and the toothbrush head 60 can be made very thin. This provides a more comfortable experience for the user of the toothbrush, which is especially important for children.

The upper part of the casing 300 contains means for supporting the pivot point 70 of the transfer member 30, so that the transfer member 30 can pivot around its pivot point 70. For example, a pin may extend through a hole 70 at the pivot point of the transfer member. Alternatively, projections from the pivot point 70 of the transfer member 30 may be rotatably supported in receiving portions on the inside of the hollow casing 300. The toothbrush head 60 and drive wheel 85 may be conveniently rotatably mounted on the casing 300, so that they rotate about axis 210. For example, a pin from the casing may project into an aperture in the drive wheel and/or the toothbrush head. Alternatively, a projection from the drive wheel and/or toothbrush head may be rotatably mounted in a supporting portion of the casing 300.

While the present invention has been described above with reference to preferred embodiments, the described embodiments are to be taken by way of example only and should not be taken to limit the spirit and scope of the invention. The described embodiments may be modified or varied in ways which will be apparent to a person skilled in the art, but which fall within the scope of the invention as defined by the appended claims.

The invention claimed is:

1. An electric toothbrush having:
    a motor;
    a cam rotatably driven by the motor and having a projecting head offset from the cam's axis of rotation; whereby in use the projecting head of the cam describes a circular motion around the cam's axis of rotation;
    an elongate transfer member for transferring motion from the cam to a toothbrush head, said transfer member having first and second ends, the first end having a receiver for receiving the projecting head of the cam, the second end having or being linked to a mechanism for transferring oscillatory motion to a toothbrush head, the transfer member having a pivot point positioned between its two ends;
    said receiver having an elongate aperture for receiving the projecting head of the cam including long sides and short sides, the length of the aperture being equal to or greater than the diameter of the circular motion of the projecting head of the cam, the width of the aperture, perpendicular to said length, having a length less than the length of said aperture; whereby in use circular motion of the projecting head of the cam causes the elongate transfer member to pivot around its pivot point to thereby convert the circular motion of the projecting head into substantially planar oscillatory motion of the transfer member by action of the projecting head of the cam against the long sides of the elongate aperture.

2. An electric toothbrush according to claim 1, wherein the width of the elongate aperture is just large enough to accommodate the projecting head of the cam.

3. An electric toothbrush according to claim 1 wherein the aperture is substantially rectangular.

4. An electric toothbrush according to claim 1, further comprising the toothbrush head linked to said mechanism for transferring oscillatory motion to the toothbrush head.

5. An electric toothbrush according to claim 1, wherein the projecting head of the cam is cylindrical.

6. An electric toothbrush according to claim 1, wherein the projecting head of the cam is substantially spherical.

7. An electric toothbrush according to claim 1 wherein the projecting head of the cam comprises a ball.

8. An electric toothbrush according to claim 1 wherein the motor has a shaft, which is connected directly to the cam, such that the axis of rotation of the motor and the cam are the same.

9. An electric toothbrush according to claim 1 wherein the mechanism for transferring oscillatory motion to the toothbrush head comprises an arrangement of interacting gear teeth.

* * * * *